United States Patent
McDaniel

(10) Patent No.: US 6,629,971 B2
(45) Date of Patent: Oct. 7, 2003

(54) PROCESS FOR STIMULATING HAIR GROWTH

(76) Inventor: David McDaniel, 3033 Little Haven Rd., Virginia Beach, VA (US) 23452

(*) Notice: Subject to any disclaimer, the term of this patent is extended or adjusted under 35 U.S.C. 154(b) by 170 days.

(21) Appl. No.: 09/819,081

(22) Filed: Feb. 15, 2001

(65) Prior Publication Data

US 2002/0123746 A1 Sep. 5, 2002

Related U.S. Application Data

(62) Division of application No. 09/203,178, filed on Nov. 30, 1998, now Pat. No. 6,283,956.

(51) Int. Cl.⁷ .............................. A61B 18/18
(52) U.S. Cl. .................. 606/9; 606/32; 606/127; 606/131; 607/88; 607/98; 607/101; 128/898
(58) Field of Search ................. 606/9–13, 16, 606/32–34, 41, 127, 128, 131–134, 187; 607/88–91, 96–101; 128/898

(56) References Cited

U.S. PATENT DOCUMENTS

| | | |
|---|---|---|
| 4,458,678 A | 7/1984 | Yannas et al. |
| 4,646,743 A | 3/1987 | Parris |
| 4,767,402 A | 8/1988 | Kost et al. |
| 4,836,203 A | 6/1989 | Muller et al. |
| 4,888,354 A | 12/1989 | Chang et al. |
| 4,930,504 A | 6/1990 | Diamantopulos et al. |
| 4,969,912 A | 11/1990 | Kelman et al. |
| 5,021,452 A | 6/1991 | Labbe et al. |
| 5,037,432 A | 8/1991 | Molinari |
| 5,071,416 A | 12/1991 | Heller et al. |
| 5,198,465 A | 3/1993 | Dioguardi |
| 5,226,907 A | 7/1993 | Tankovich |

(List continued on next page.)

FOREIGN PATENT DOCUMENTS

ZA 97/7751 8/1997

OTHER PUBLICATIONS

Wei Yu et al. "Improvement of Host Response to Sepsis by Photobiomodulation" Lasers in Surgery and Medicine, 21:262–268, 1997.

Abergel et al., "Biostimulation of Wound Healing by Lasers: Experimental Approaches in Animal Models and in Fibroblast Cultures" J. Dermatol. Surg. Oncol., 13:2, Feb. 1987.

Van Breugel et al., "Power Density and Exposure Time of H–Ne Laser Irradiation are More Important than Total Energy Dose in Photo–Biomodulation of Human Fibroblasts in Vitro" Lasers in Surgery and Medicine, 12:528–537, 1992.

Sumian et al., "A New Method to Improve Penetration Depth of Dyes into the Follicular Duct: Potential Application for Laser Hair Removal".

Primary Examiner—Linda C. M. Dvorak
Assistant Examiner—Ahmed Farah
(74) Attorney, Agent, or Firm—Morrison & Foerster LLP

(57) ABSTRACT

A method for producing preferential damage to hair exiting mammalian skin. A agent having an average diameter for enabling the agent to penetrate the hair duct is selected. The agent is designed to attach to, or become physically incorporated into, the hair shaft, the hair follicle, the hair bulb or the hair duct. The agent has an electromagnetic radiation absorption characteristic which enables the agent to absorb a first wavelength of electromagnetic radiation from a skin-penetrating electromagnetic radiation source, such as a laser. The agent is applied to the skin so that the agent penetrates the skin and attaches to or becomes physically incorporated into the hair shaft, the hair follicle, the hair bulb or the hair duct. The agent is exposed to the first wavelength of electromagnetic radiation and absorbs the first wavelength of electromagnetic radiation.

4 Claims, 5 Drawing Sheets

U.S. PATENT DOCUMENTS

| | | |
|---|---|---|
| 5,231,975 A | 8/1993 | Bommannan et al. |
| 5,266,480 A | 11/1993 | Naughton et al. |
| 5,332,802 A | 7/1994 | Kelman et al. |
| 5,366,498 A | 11/1994 | Brannan et al. |
| 5,397,352 A | 3/1995 | Burres |
| 5,423,803 A | 6/1995 | Tankovich et al. |
| 5,425,728 A | 6/1995 | Tankovich |
| 5,445,146 A | 8/1995 | Bellinger |
| 5,445,634 A | 8/1995 | Keller |
| 5,460,939 A | 10/1995 | Hansbrough et al. |
| 5,591,444 A | 1/1997 | Boss, Jr. |
| 5,620,478 A | 4/1997 | Eckhouse |
| 5,643,334 A | 7/1997 | Eckhouse |
| 5,647,866 A * | 7/1997 | Zaias et al. .................... 606/9 |
| 5,658,323 A | 8/1997 | Miller |
| 5,660,836 A | 8/1997 | Knowlton |
| 5,660,850 A | 8/1997 | Boss, Jr. |
| 5,665,372 A | 9/1997 | Boss, Jr. |
| 5,669,916 A | 9/1997 | Anderson |
| 5,752,949 A * | 5/1998 | Tankovich et al. ............ 606/9 |
| 5,755,752 A | 5/1998 | Segal |
| 5,766,214 A * | 6/1998 | Mehl, Sr. et al. ............... 606/9 |
| 5,817,089 A | 10/1998 | Tankovich et al. |
| 5,843,072 A | 12/1998 | Furumoto et al. |
| 6,050,990 A * | 4/2000 | Tankovich et al. ............ 606/9 |
| 6,074,382 A | 6/2000 | Asah et al. |

* cited by examiner

PROCESS FOR STIMULATING HAIR GROWTH

This is a divisional application of U.S. application Ser. No. 09/203,178, filed Nov. 30, 1998 now issued as U.S. Pat. No. 6,283,956.

FIELD OF THE INVENTION

The present invention generally relates to a system for the reduction, elimination or stimulation of hair growth in mammalian skin.

BACKGROUND OF THE INVENTION

There are several known techniques for attempting to reduce, eliminate or stimulate hair growth in human skin. A few of these known techniques are scientifically proven and widely accepted as effective. However, their degree of efficacy varies greatly.

There are several processes which may be used for producing preferential damage of the hair. In one process the target may be natural melanin pigment in the hair shaft and surrounding supporting tissues. In another process the target may be an external chromophore or contaminant. Most of these processes tend to damage the hair, either by producing heat or by photo-acoustical shock waves. These known processes have varying degrees of effectiveness, but require multiple treatments and, in their current form, produce only partial permanent hair reduction.

In recent years the use of light sources to reduce or eliminate unwanted hair growth has been developed. One known technique selects a wavelength of laser light that is well-absorbed by the naturally occurring "native" pigments in the hair shaft (and perhaps some pigment in parts of the hair duct or hair follicle cells).

Another known technique uses a short pulsed laser to produce a wavelength that may be absorbed by a "foreign" material or "skin contaminant". Aspects of this technique are described, for example, in U.S. Pat. Nos. 5,423,803, 5,817,089, 5,425,728, 5,226,907, and 5,752,949, all of which are incorporated by reference. This contaminant may be applied directly onto the skin and may be introduced into the empty space surrounding the hair shaft. One contaminant that has been used is carbon graphite in particulate form. The graphite particles have a diameter that is small enough to enable the particles to drop from the surface of the skin into the free empty spaces between the duct and the hair shaft. The energy from a laser may then interact with the contaminant particles. This causes injury to surrounding tissues whose function is to support the growth of the hair shaft. This tends to reduce or eliminate hair growth.

These contaminant particles are not physically incorporated into the hair shaft or into the surrounding hair follicle, hair bulge or hair duct cells. Nor do these contaminant particles chemically, immunologically, biologically or otherwise interact, react or complex with the hair shafts or tissue cells. The contaminant particles simply physically occupy the space surrounding the hair shaft.

Another known hair removal technique is to use a pulsed electromagnetic radiation source to produce a wavelength that may be absorbed by hair, as described, for example, in U.S. Pat. No. 5,683,380, which is incorporated by reference.

There are problems with present light and laser hair removal techniques. Known melanin targeting systems work reasonably well and are reasonably safe only when the color of the hair is very dark and when the skin is very light and not tanned. Virtually all light sources which tend to target melanin are also inherently absorbed by the overlying and surrounding skin. At present, these light sources cannot be safely used at optimal very high power settings for people with darker skin or even people with a dark tan.

Dying the hair allows increased damage to the hair target, helps confine damage to the hair target, and enables the use of power settings that are not so high as to damage surrounding and overlying skin. Treatments which target melanin inherently do not work well on light hair, since there is not enough natural pigment to absorb enough energy to damage hair even if the power is quite high. Using hair dye enables this obstacle to be overcome.

A known hair removal process which uses a 1064 nm laser to produce a wavelength that may be absorbed by a skin contaminant appears to be safe on all skin colors, including darker skin colors. However, this safety is a consequence of there being very little melanin absorption. It is therefore necessary to add graphite particles in oil contaminant lotion before laser treatment. This graphite particle lotion does not enter into the hair shaft itself. Instead, the graphite lotion tends to occupy empty spaces surrounding the hair shaft as it sits in the hair duct. This presents a problem. Either an insufficient or sub-optimal number of graphite particles penetrate into the hair duct, or an insufficient amount of damage is caused by the graphite particles. Consequently, many treatments tend to be required before an acceptable result is achieved.

SUMMARY OF THE INVENTION

The present invention enables the safe treatment of virtually all hair colors (including light hair) on virtually all skin colors (including light, untanned skin).

The present invention may be advantageously used with virtually any laser or light mediated hair removal device or process. The present invention tends to enhance damage to unwanted hair without significantly increasing adverse side effects or compromising safety. The present invention enables the use of existing light sources, by selecting a dye which is well absorbed by that light source.

The present invention encompasses all dyes or agents which may, by any mechanism, be attached or incorporated into the hair shaft or the hair duct cells or any part of the hair follicle cells or cells of the supporting tissues, including blood vessels supplying the hair follicle. These agents, and their breakdown products, are preferably non-toxic. Each agent may be appropriately matched to a corresponding light source.

The present invention may be used in conjunction with known laser or light sources. The present invention, in a preferred embodiment, tends to enhance laser or light activated hair removal. The present invention encompasses using one process to treat hair, and then going back over the area (or simultaneously) treating with two different light sources or simultaneously treating with single or multiple sources.

The present invention, in a preferred embodiment, is able to enhance virtually any hair removal process. Enhancement may occur, for example, by enabling more hair to be removed, or by eliminating hair for a longer period of time, or by increasing the probability (or percentage) of hairs that are permanently destroyed.

BRIEF DESCRIPTION OF THE DRAWINGS

A detailed description of a preferred embodiment of the present invention will be made with reference to the accompanying drawings.

DETAILED DESCRIPTION OF THE PREFERRED EMBODIMENTS

Figure 1:
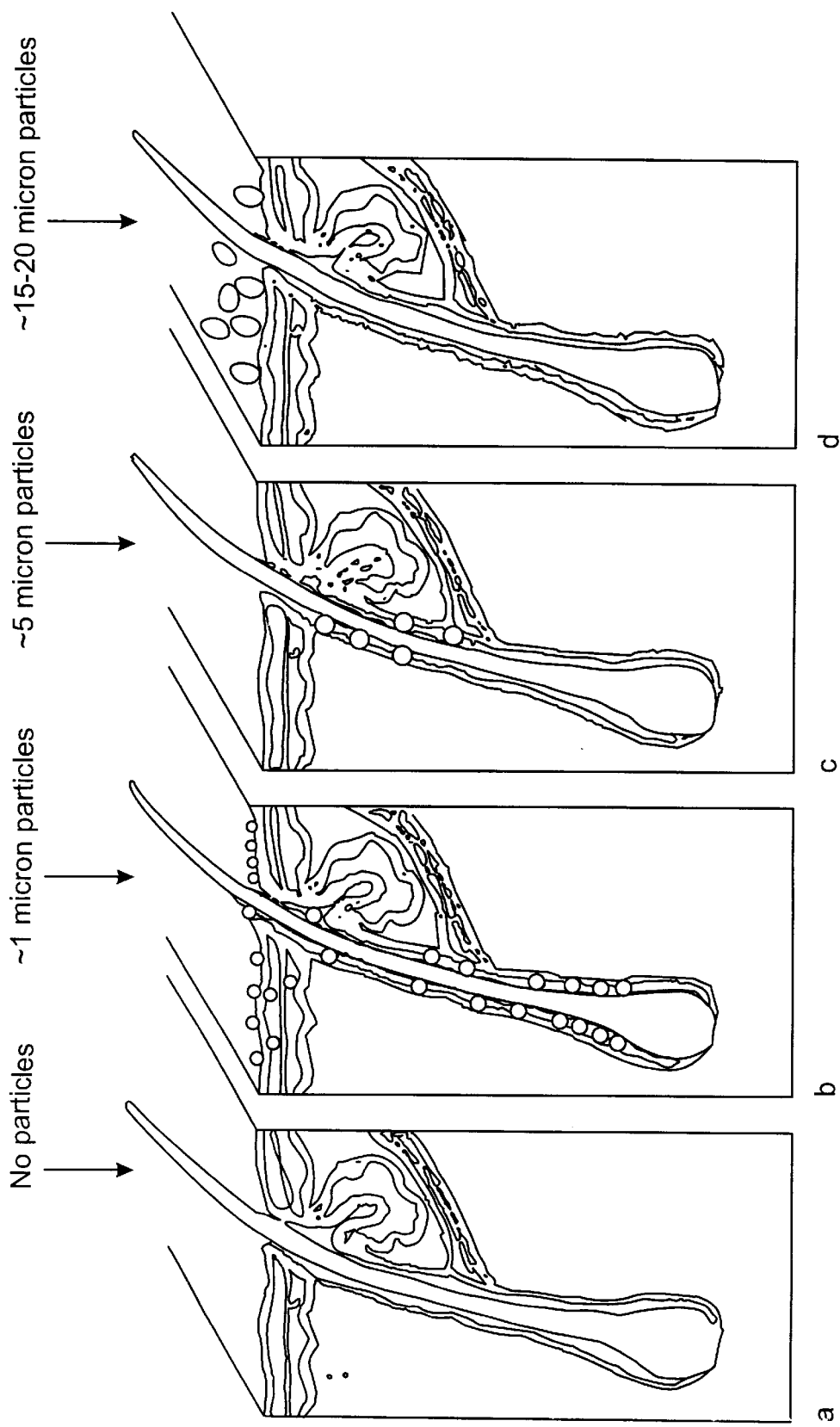
FIG. 1a illustrates an example of a hair duct and sebaceous glands without any particles being present.
FIG. 1b illustrates an example of a distribution of particles having an average diameter of about one micron in a hair duct and sebaceous glands.
FIG. 1c illustrates an example of a distribution of particles having an average diameter of about five microns in a hair duct and sebaceous glands.
FIG. 1d illustrates an example of a distribution of particles having an average diameter of about fifteen to twenty microns in a hair duct and sebaceous glands.
Figure 2:
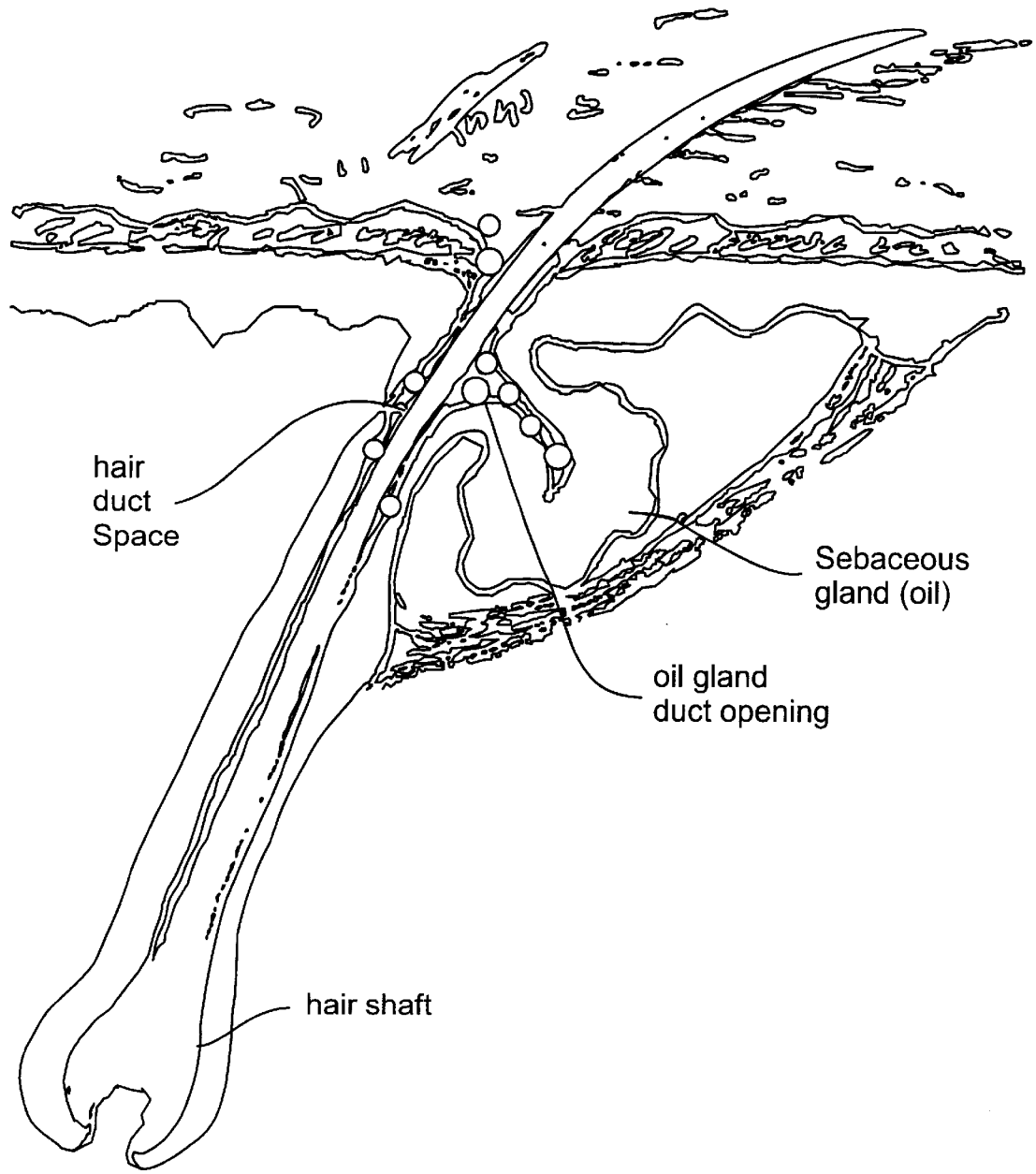
FIG. 2 illustrates, in an enlarged view, an example of a distribution of particles having an average diameter of about five microns in a hair duct and sebaceous glands.
Figure 3:
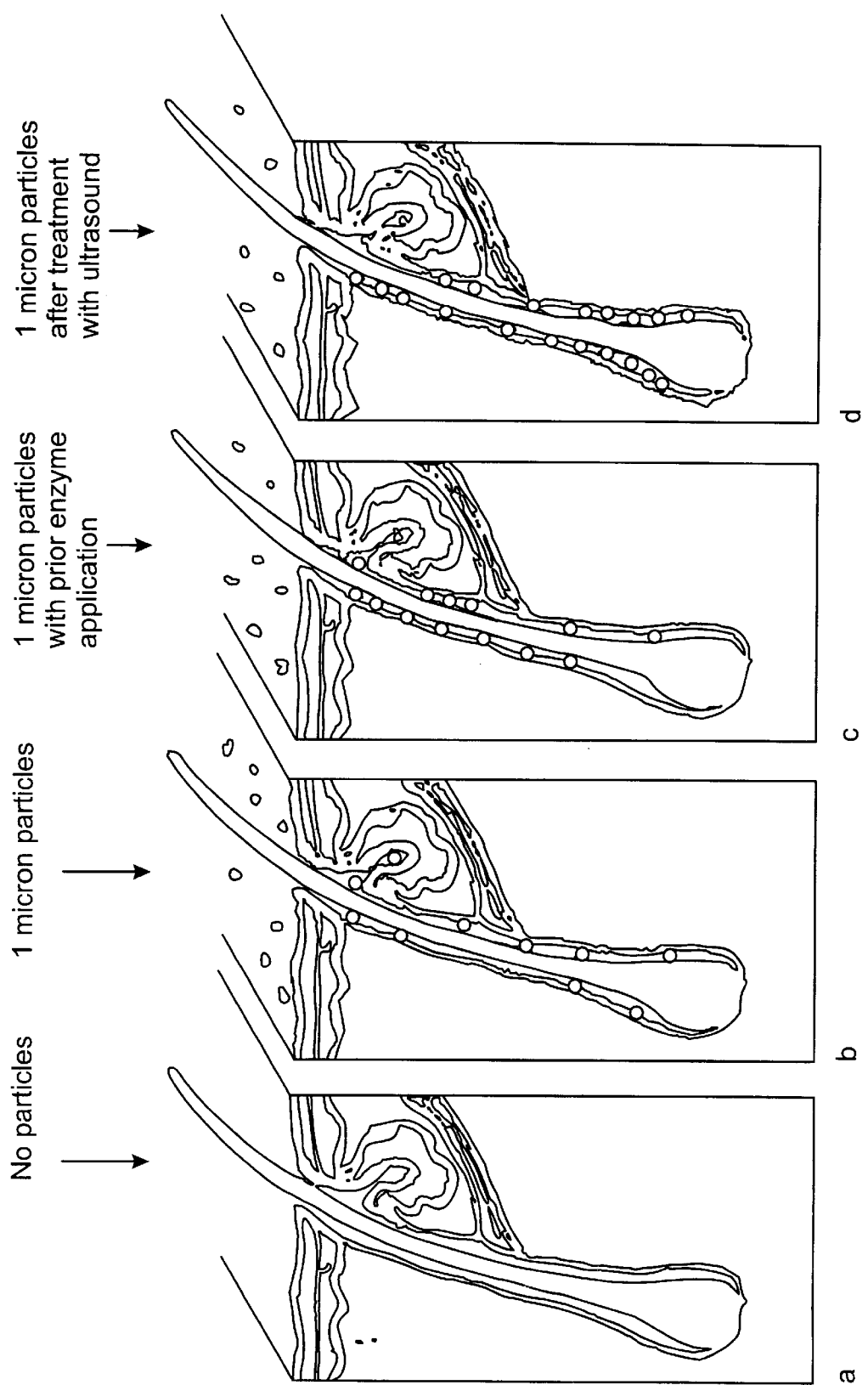
FIG. 3a illustrates an example of a hair duct and sebaceous glands without any particles being present.
FIG. 3b illustrates an example of a distribution of particles having an average diameter of about one micron in a hair duct and sebaceous glands
FIG. 3c illustrates an example of a distribution of particles having an average diameter of about one micron in a hair duct and sebaceous glands in which an enzyme has been used to help "unplug" hair follicle openings, thus allowing more particles to penetrate.
FIG. 3d illustrates an example of a distribution of particles having an average diameter of about one micron in a hair duct and sebaceous glands in which ultrasound treatment has been used to increase the number of particles in the hair duct and enabled the particles to penetrate the deeper part of the hair duct.
Figure 4:
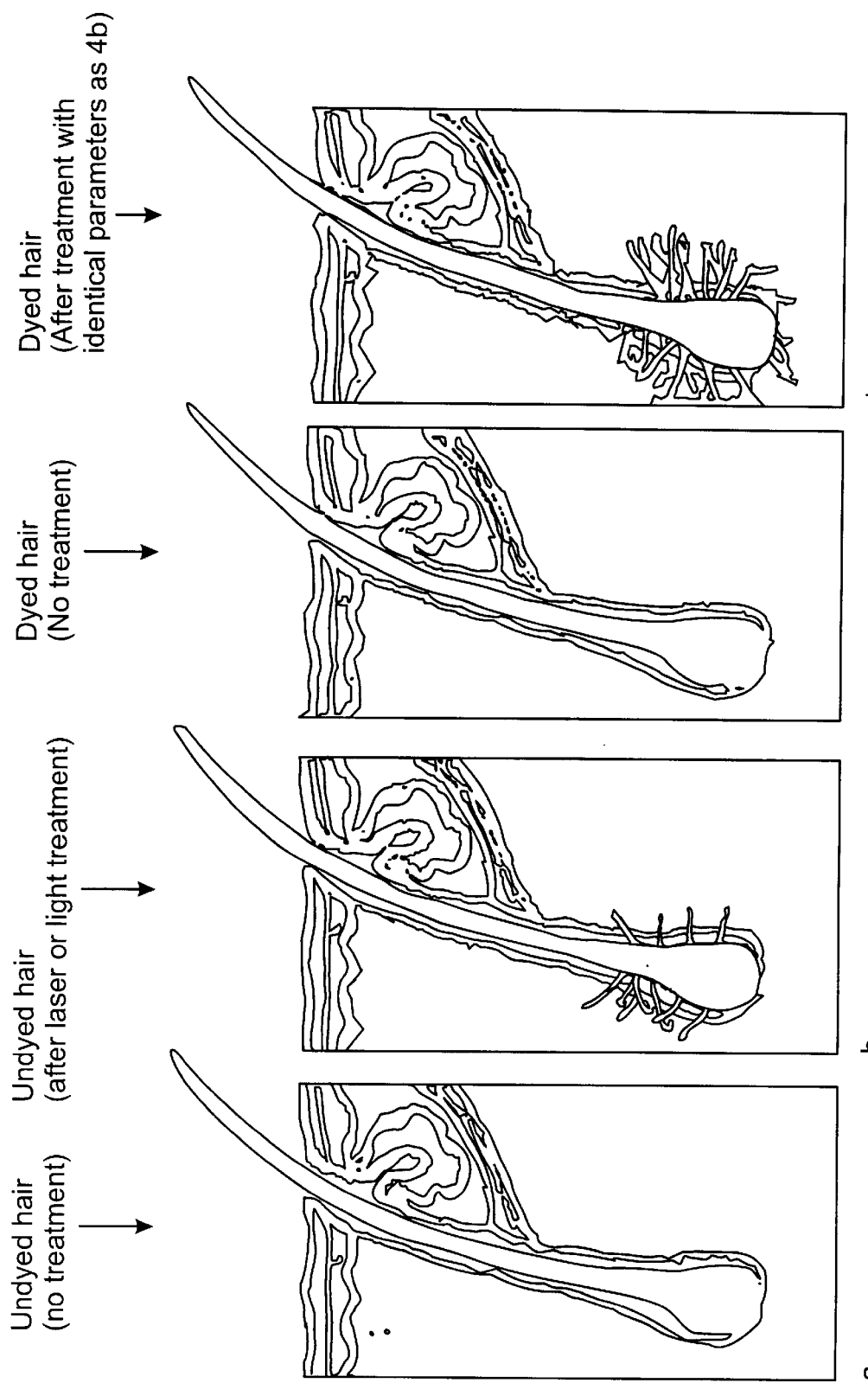
FIG. 4a illustrates an example of a hair duct and sebaceous glands prior to hair dying treatment.
FIG. 4b illustrates an example of a hair duct and sebaceous glands prior to hair dying treatment and after laser or light treatment.
FIG. 4c illustrates an example of a hair duct and sebaceous glands after hair dying treatment.
FIG. 4d illustrates an example of a hair duct and sebaceous glands after hair dying treatment and after laser or light treatment using parameters substantially identical to those used in the example illustrated in FIG. 4b. The example illustrated in FIG. 4b shows less damage than the example illustrated in FIG. 4d after otherwise identical treatment.
Figure 5:
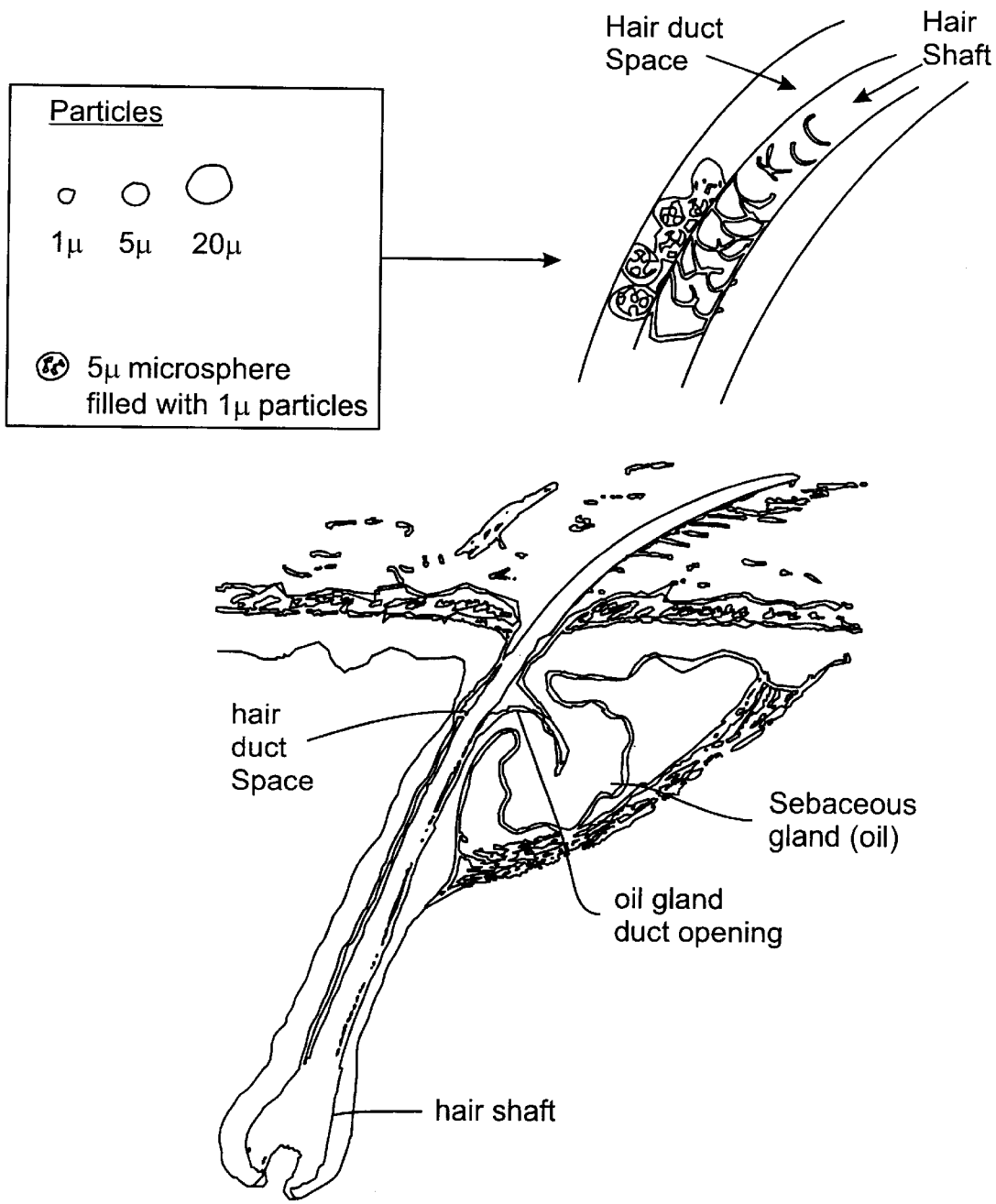
FIG. 5 illustrates, in an enlarged view, an example of a distribution of particles having an average diameter of about one micron encapsulated in microspheres having an average diameter of about five microns in a hair duct and sebaceous glands.

The following detailed description is of the best presently contemplated mode of carrying out the invention. This description is not to be taken in a limiting sense, but is made merely for the purpose of illustrating the general principles of the invention. The scope of the invention is best defined by the appended claims.

In a preferred embodiment, the present invention is directed to a process for producing temporary or permanent reduction or removal, in human or mammalian skin, of some or all of the hairs growing in hair follicles and exiting the skin through hair ducts. In a preferred embodiment the process produces little or no permanent injury or damage to nearby skin tissue. Substantially only the hair follicle and immediately surrounding tissue are damaged.

In a process according to one embodiment of the present invention, an agent may be selected which is capable of penetrating the hair ducts and attaching, bonding or otherwise becoming incorporated into the hair shaft, hair follicle, hair bulb or hair duct cells. The agent may be characterized as an active agent in that it performs a function in addition to simply occupying or contaminating the space in the ducts surrounding the hair shaft. The agent may have sufficient optical absorption of a wavelength (or a combination of wavelengths) of a coherent or non-coherent light source which can penetrate the skin adequately to be absorbed by the target agent or the new agent-tissue complex.

The area of skin from which unwanted hair is to be removed may be cleansed. After the skin is cleansed, the hair and/or the skin may be treated to improve permeability. This may be accomplished, for example, by treating the hair and/or skin with steam or a hot moist towel to hydrate the skin and hair.

The agent may be applied in sufficient quantity and in suitable form to be incorporated into the target tissue in adequate or optimal amounts to allow the production of the desired tissue effect.

Excess agent may be removed, neutralized, inactivated, decolorized, diluted or otherwise altered so that residual contamination of the skin or hair duct space by such excess agent is either (a) absent and does not interact with the light or energy source, or (b) present in such small quantity that it provides no clinical effect.

Delivery of the desired agent into the target tissues may be enhanced, facilitated or made possible by the use of enzymes or by the use of ultrasound or phonophoresis either for penetration into the hair duct or the hair follicle or hair bulb cells or to penetrate into the hair shaft itself or surrounding target tissues or to cause the release of the agent from the encapsulated delivery device such as liposomes, polymers, microspheres, etc. so as to cause penetration or attachment of this active agent. The water content or absorption by the hair shaft might be enhanced, to increase the hair shaft diameter and volume or to otherwise enhance the process.

Ultrasound may be used therapeutically to interact directly with the agent or the agent-tissue complex to produce the desired damaged target tissues (to be used alone or in combination with laser or non-laser light sources). Ultrasound may be used to make graphite penetrate better, for example. A more detailed description of several aspects of the use of ultrasound may be found, for example, in the applicant's co-pending U.S. patent application Ser. No. 09/087,146 for "Ultrasound Enhancement of Percutaneous Drug Absorption."

Although preferred embodiments of the present invention may use ultrasound and/or laser or light energy, the present invention is not limited to the use of these energy sources. Other sources of energy, including (without limitation) microwave energy and radio frequency energy may also be used.

The targeted skin may be exposed to one or more wavelengths of laser or non-laser light or single or multiple frequencies of ultrasound. A variety of parameters may be used (including pulse duration, energy, single or multiple pulses, the interval between pulses, the total number of pulses, etc.) to deliver sufficient cumulative energy to interact with the agent or tissue complex. This may result in injury, damage or destruction of the hair follicle, hair bulb or the supporting skin tissue, thereby delaying regrowth of the hairs, or diminishing the hair shaft diameter, or miniaturizing the hair follicles or completely destroying these tissues, resulting in permanent hair removal. Ultrasound may also be used to preheat the target structures, the skin, and/or the hair.

The agent may be incorporated into the target tissue by a variety of mechanisms. These mechanisms include, but are not limited to: 1) physical incorporation into the hair shaft or target tissue cells while leaving the chemical structure essentially unaffected, or 2) undergoing a chemical reaction resulting in a new agent-tissue complex which then becomes a target for energy absorption.

The process may be a single or multi-step process and may involve the use of cofactors, catalysts, enzymes, or multiple agents which interact to ultimately become or create an active agent or agent-tissue complex.

Agents may include, without limitation: hair dyes, vegetable dyes, food coloring, fabric dyes, tissue stains, shoe or leather dyes, other plant products (such as flavonols, chlorophyll, carotenoids, enzymes, monoclonal antibodies, any immunological agent, genetically engineered agent, benign infectious agents, whether naturally occurring or genetically engineered (e.g. the bacteria that normally reside on the skin such as acne bacteria, etc.), antibiotics, agents which attach to melanin in the hair shaft or surrounding follicle, bulge or duct cells directly, whether by topical or systemic agents that localize in the target tissues.

Agents may be delivered in pure form, in solution, in suspension, in emulsions, in liposomes, in synthetic or natural microspheres, microsponges or other known microencapsulation vehicles.

The process may include an application of an active agent and treatment with an energy source as a single treatment. Alternatively, treatment with an energy source may be delayed for hours or days after application of an active agent. Application of an active agent may be performed or applied at another location, such as patient's home, prior to the energy treatment.

After an energy treatment has occurred it may be desirable in some situations to remove, neutralize, decolorize or otherwise inactivate any residual active agent.

One preferred embodiment uses a hair dye incorporated into the hair shafts. The dye may be selected to absorb 1064 nm laser light. Depending upon the wavelength of laser light, suitable hair dyes may include, for example, Professional Miss Clairol 52D Black Azure or 51D Black Velvet. Laser pulse durations may be selected with sufficient power density to allow the target tissue to be appropriately damaged.

One known hair removal process uses a solution of graphite in oil lotion and a Q-switched 1064 nm Nd:YAG laser. The solution may be applied to the skin and hair and then the skin and hair may be treated with the laser using known parameters. It may be preferable to use a high repetition rate, such as 8–10 Hertz or higher, and move the laser handpiece slowly enough that pulses are "stacked" in one spot for several pulses before the handpiece is moved to an adjacent spot. It has been found that there is a stair-step like effect of incremental temperature rise in the dyed hairs with the second and third pulses versus a single pulse. A faster repetition rate also tends to help build the heat up faster, and to higher levels. This tends to produce the maximum heat (which is desirable, as long as the heat stays confined to the hair follicle and the immediately adjacent supporting tissues). Since this effect occurs substantially simultaneously with other destructive effects of the process, the damage to hair growth tends to be enhanced. Unlike carbon exploded particles on light impact, the dyes and similar agents may actually remain absorbing for a brief time until they reach a critical temperature at which time they are destroyed or become non absorbers, thus acting as a sort of heat sink for a brief time, allowing more heat to accumulate. Safety remains at about the same level, since dye related damage tends to be confined to target tissues. There is no appreciable change in treatment time.

In an alternative embodiment, a hair dying process similar to that described above may be used with a laser that tends to target melanin rather than graphite contaminant. Such a laser may be, for example, a long pulsed alexandrite or long pulsed ruby or diode laser. In the case of a long pulsed alexandrite laser, tests have been conducted using a Cynosure LPIR version at 755 nm wavelength and 20 $J/cm^2$ and 20 msec pulse duration with a dye that absorbs at 755 nm. Infrared camera analysis of hair treated according to this process shows both relatively higher temperature and also relatively slower cooling of the hair shafts themselves. This allows further heating of the target tissues. It also helps make the treatment safer and probably more effective.

Another preferred embodiment uses a longer pulsed laser in the 750 nm–1000 nm range and appropriate parameters to achieve the desired tissue damage goal.

Another embodiment uses a tissue dye which attaches to, or is incorporated into, a target cell and surrounding tissues. The target tissue may be illuminated with a multi-wavelength non-laser light source using appropriate parameters to achieve the desired tissue damage goal.

Another embodiment uses a light source which is well-absorbed by the melanin naturally present in undyed darker hairs and a hair dye which may be incorporated into the hair shaft. The hair dye will be well-absorbed by the same wavelength of light (or alternatively two or more wavelengths, one for melanin and one or more for the dye) which is absorbed by the undyed hair, resulting in an enhanced or greater injury to the target tissue (or permitting lower treatment energy parameters, resulting in safer treatment than if the hairs were treated without the hair dye). This tends to benefit people having darker skin or tanned skin, by allowing lower treatment energy. For example, a diode laser or LED or non-laser light source could produce a continuous or pseudo-continuous beam of light energy using pulse durations as long as seconds at a wavelength which is absorbed by the native hair pigment and also by the hair dye used. A pulse duration on the order of between about one and thrity seconds appears to be preferable. This also tends to be a much longer time than is used in most systems in use today.

Another embodiment uses an agent which facilitates cavitation shock waves or a thermal effect, or both. This preferentially damages (or stimulates) the target tissues while minimizing damage (or other adverse effects) on surrounding non-target tissues. This may be used with very short pulsed lasers or light sources or with ultrasound alone.

In one embodiment a process in accordance with the present invention may be used to temporarily or permanently stimulate hair growth in human or mammalian skin. Some or all of the hair follicles in the treatment area may be stimulated to grow, to have their growth cycle accelerated, to prolong the hair growth cycle, to increase the hair shaft diameter, to change the hair shaft color, to stimulate hairs that are in a dormant state or which originate from an area of hair loss or baldness, or to produce a combination of the above-mentioned effects. This tends to involve a lower level of delivered energy than that used for hair reduction. Phonophoresis may be used to deliver other stimulating or growth supporting agents.

In one embodiment a process in accordance with the present invention may be used to provide short or long-term control, improvement, reduction or elimination of acne or other skin diseases. An active agent may be physically or chemically or immunologically incorporated into cells of the sebaceous (oil) glands or into the naturally occurring acne bacteria, yeast or similar organisms which feed on the oil in the oil glands (or sweat glands)or are otherwise relatively benign inhabitants. Improvement in skin disorders may be a direct or indirect result of the application of the agents in this process, as may reduced oiliness of the skin, reduced size or diminished appearance of pores, etc.

Other similar disorders such as folliculitis which involve the pilo-sebaceous (hair/oil gland) unit may also be treated using the present invention. The present invention may also be used to reduce perspiration, sweating, or hyperhidrosis from eccrine (sweat) glands or apocrine glands. A preferred embodiment of the present invention may be used to treat other skin disorders such as, for example, viral warts, psoriasis, precancerous solar keratosis or skin lesions, hyperhidrosis/excessive sweating, and perhaps skin ulcers (diabetic, pressure, venous stasis).

A preferred embodiment of the present invention may use various microencapsulation processes to deliver active agents. If the diameter of the micro encapsulations is about five microns, then there may be relatively site specific preferential delivery into the sebaceous oil glands or skin surface stratum corneum cells. If the diameter of the microencapsulations is in the range of about one micron, then the active agents may be delivered with a more random distribution between the hair ducts and the oil glands. If the diameter of the microencapsulations is larger, on the order of about 20 microns or greater, then delivery will tend to be restricted primarily to the skin surface. The micro encapsulations may be synthetic or natural. If ultrasound is used to enhance penetration, then the diameters and ultrasound treatment parameters may need to be adjusted according to the applicable principles which allo the estimation of the optimal ultrasound parameters for driving small particles into the skin, skin appendages or skin orifices.

Microencapsulation may be used to improve delivery of known agents such as indocyanine green and particles of carbon or graphite. A known technique for using a laser to produce a wavelength that may be absorbed by indocyanine green for a hair removal treatment process is described, for example, in U.S. Pat. No. 5,669,916, which is incorporated by reference. It has been found that by using smaller particles and putting the smaller particles into more uniform diameter microencapsulations, more site specific or uniform targeting may be achieved. A preferred formulation may include indocyanine green or other dyes or agents to form a lipid complex which is fat-loving (lipophilic). The delivery and clinical effects of agents and dyes such as indocyanine green dye may be refined and enhanced by selecting a carrier or encapsulation having a diameter that increases the probability of preferential delivery to a desired space, and/or that enables interaction with ultrasound to thereby increase the probability of preferential delivery, and/or that selectively attaches to the sebaceous gland and/or hair.

Indocyanine green dye is presently in medical use, appears to be relatively benign, may be activated by red visible lasers (in the 800 nm range) may penetrate deeply enough to reach the oil glands, is used for leg vein and hair removal, and is relatively safe, cheap, and reliable. A known technique for using a laser to produce a wavelength that may be absorbed by indocyanine green for use in a leg vein treatment process is described, for example, in U.S. Pat. No. 5,658,323, which is incorporated by reference.

The microsponges containing the active agent may selectively attach, or at least have a chemical affinity for, some part of the oil gland. The ICN dye may be conjugated with lipids, which would then have an affinity for the oil glands. Alternatively, the attachment may occur after the active agent is released from the microsponge, either passively or by attractive or chemical forces. In the case of some microencapsulation carrier vehicles, release may occur after disruption of the vehicle integrity itself, possibly by ultrasound or laser or light or other energy source or perhaps a chemical reaction.

In a preferred embodiment the ICN dye may be mixed with lipids, or put into microsponges (a.k.a. microspheres), and then applied to the skin surface, allowed to sit for a time. Excess dye may be removed, and then the area may be treated with laser light at about 800 nm, between about 0.1 and 100 millisec pulses and around 1.0–10.0 Joules/cm$^2$.

U.S. Pat. No. 5,817,089 specifies "particles having a major diameter of about 1 micron". It has been discovered, however, that these diameters may not be optimal. A 1993 Pharmaceutical Research journal article by Rolland et al describes an acne treatment wherein a topical acne drug is delivered with less irritation by putting the drug into synthetic polymer microsphere sponges. This article reported that an optimal diameter for site-specific delivery into sebaceous oil glands in the skin was about 5 microns, and that 1 micron particles randomly delivered to the hair follicle and stratum corneum.

Most agents may not inherently be the optimal size. However, virtually any agent may be preferentially delivered to the sebaceous glands by either synthetic microspheres, or liposomes, or albumen microspheres, or other similar "delivery devices".

In a preferred embodiment for treatment of acne, graphite particles having an average diameter of about one micron may be placed in delivery devices, such as microsponges, having an average diameter of about five microns. The microsponges may then be suspended in a lotion. Ultrasound may be used to drive the particles into the skin. The optimal ultrasound parameters may be based on the outside particle diameter (especially if particles are uniform). Selective delivery of the particles to hair and perhaps to sweat glands may be improved.

Use of such applications could enable selective delivery of anti-acne agents, or hair dye for laser hair removal, or agents which stimulate hair growth, or other hair treatments, where the encapsulation diameter was used, with or without ultrasound, to preferentially deliver, and ultrasound at different parameters or laser was used to release (not necessarily to activate or interact).

These techniques may be applied to many other agents in addition to ICN dye and graphite lotions. The term "encapsulated delivery device" is used herein as a generic term which encompasses all such possible items.

Pressure may be used to impel particles (i.e., graphite, carbon, or other active agent or skin contaminant particulates) into the skin, either in the spaces between the stratum corneum, into the hair ducts and hair follicles, the sebaceous oil glands, or other structures. Air pressure or other gases or liquids may be used to enhance delivery-or increase the quantity of delivered agent. A known technique for using an air pressure device for removing skin surface is described, for example, in U.S. Pat. No. 5,037,432, which is incorporated by reference.

Ultrasound may be used to physically deliver hair dye and to enhance penetration into the hair shaft itself (see, for example, U.S. Pat. No. 5,817,089, incorporated herein by reference). The use of ultrasound to physically drive graphite particles down for the treatment of unwanted hair or acne appears to have been suggested in the prior art. However, the applicant is aware of no prior art disclosure or suggestion of: (1) the use of ultrasound to enhance the penetration of an agent into the hair shaft itself, or into surrounding cells, or (2) the use of ultrasound to drive graphite particles into spaces between the stratum corneum to enhance the effects of a skin peel process (which physically removes a portion of the outer layers of the skin surface).

A known skin peel process may be improved by using ultrasound to open intercellular spaces in the outer stratum corneum layer of the skin via cavitation. Then a graphite lotion may be driven in further with the same or similar ultrasound. Fibroblast stimulation may be optimized with both topical agents that are applied afterwards (while the skin is still relatively permeable) and also with additional low level laser stimulation.

The processes described above may be used to deliver two different agents, either serially or simultaneously. The two agents may then be activated by the laser together to work synergistically, or to combine and then have an effect, or to deliver two different agents that may be activated simultaneously or very closely in time.

Two entirely different laser or light beams may be delivered substantially simultaneously through the same optics at different parameters. For example, one beam may be delivered primarily to release or to activate, and a second beam primarily to treat. Additive effects may be achieved by using two beams at the same time. For example, a known process for skin peel and hair reduction may be optimal at 1064 nm for safety and for treating all skin colors, but other wavelengths may be better to achieve a low level laser stimulation of fibroblasts. The same laser handpiece may deliver the known process for skin peel and hair reduction, and either simultaneous or synchronized sequentially in time deliver another wavelength that may be optimal to complement. In the one case it may be the best wavelength to stimulate fibroblasts. In another case it may allow selection of a hair dye (or other agent) having very strong affinity for hair and very strong absorption.

The presently disclosed embodiments are to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A process for stimulating growth of hair exiting mammalian skin through a hair duct, the process comprising:

selecting at least one of a photoactive agent and a photo sensitizing agent, the agent having an average diameter enabling the agent to penetrate the hair duct, the agent having an electromagnetic radiation absorption characteristic enabling the agent to absorb at least a first wavelength of electromagnetic radiation from a skin-penetrating electromagnetic radiation source, applying the agent to the hair and skin, forming an agent-tissue complex by a process comprising reacting the agent with cells in the hair, the skin, or both, and exposing the agent-tissue complex to incoherent, multi-frequency electromagnetic radiation comprising at least the first wavelength of electromagnetic radiation, whereby the agent-tissue complex absorbs the first wavelength of electromagnetic radiation.

2. The process of claim 1, comprising the step of exposing at least one of the skin and hair to at least one external enzyme.

3. The process of claim 1, comprising the step of exposing at least one of the skin and hair to ultrasound.

4. The process of claim 1, wherein the step of exposing the agent to at least a first wavelength of electromagnetic radiation comprises exposing the agent to electromagnetic radiation from at least one of a diode laser, a light emitting diode, a filamentous incoherent light source and a non-laser light source.

* * * * *